US011311876B2

(12) United States Patent
Yang et al.

(10) Patent No.: US 11,311,876 B2
(45) Date of Patent: Apr. 26, 2022

(54) SINGLE-CELL ANALYSIS CHIP FOR ANTICANCER DRUG COMBINATION (71) Applicant: GWANGJU INSTITUTE OF SCIENCE AND TECHNOLOGY, Gwangju (KR)

(72) Inventors: Sung Yang, Gwangju (KR); Jong Chan Choi, Gwangju (KR)

(73) Assignee: GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 96 days.

(21) Appl. No.: 16/629,912

(22) PCT Filed: Jul. 10, 2018

(86) PCT No.: PCT/KR2018/007819
§ 371 (c)(1),
(2) Date: Jan. 9, 2020

(87) PCT Pub. No.: WO2019/013531
PCT Pub. Date: Jan. 17, 2019

(65) Prior Publication Data
US 2021/0078000 A1 Mar. 18, 2021

(30) Foreign Application Priority Data
Jul. 11, 2017 (KR) .................. 10-2017-0088069

(51) Int. Cl.
*B01L 3/00* (2006.01)
*G01N 21/64* (2006.01)
(Continued)

(52) U.S. Cl.
CPC ........ *B01L 3/502715* (2013.01); *G01N 21/64* (2013.01); *G01N 33/5011* (2013.01); *G01N 33/68* (2013.01)

(58) Field of Classification Search
CPC ........ B01L 3/502715; B01L 3/502753; B01L 3/502761; B01L 3/502738;
(Continued)

(56) References Cited

U.S. PATENT DOCUMENTS

2009/0035792 A1    2/2009 Singh et al.
2011/0275097 A9*  11/2011 Singh ................. G01N 33/5041
                                                            435/7.23
(Continued)

FOREIGN PATENT DOCUMENTS

KR    1020090035401 B1    4/2009
KR    1020100060471 B1    6/2010
(Continued)

OTHER PUBLICATIONS

PCT/KR2018/007819. International Search Report & Written Opinion (dated Jan. 17, 2019). 15 pages.
(Continued)

*Primary Examiner* — Jennifer Wecker
*Assistant Examiner* — Oyeleye Alexander Alabi
(74) *Attorney, Agent, or Firm* — Loza & Loza, LLP; Heidi Eisenhut (57) ABSTRACT

An analysis chip for determining an efficient anticancer drug or anticancer drug combination for cancer cells, according to an embodiment of the present disclosure, includes a chamber which is a unit for analyzing single cancer cells, and a plurality of valves configured to regulate a fluid to be injected into the chamber, wherein the chamber includes a channel through which a fluid including an anticancer drug and a cell lysis buffer flows, a cell sorting part configured to focus cancer cells flowing along the channel, a cell capturing part configured to focus the cancer cells focused by the cell storing sorting part, and an antibody array configured to
(Continued)

capture proteins secreted from the captured cancer cells and intracellular protein through cell lysis.

8 Claims, 11 Drawing Sheets

(51) Int. Cl.
*G01N 33/50* (2006.01)
*G01N 33/68* (2006.01)

(58) Field of Classification Search
CPC ......... B01L 2200/0668; B01L 2200/10; G01N 21/64; G01N 33/5011; G01N 33/68; G01N 33/543; G01N 33/53; G01N 2021/6439; G01N 21/6428; G01N 35/085
See application file for complete search history.

(56) References Cited

U.S. PATENT DOCUMENTS

| | | | | |
|---|---|---|---|---|
| 2015/0232942 | A1* | 8/2015 | Abate | B01L 3/502784 506/9 |
| 2016/0025761 | A1* | 1/2016 | West | G01N 15/1056 506/7 |

FOREIGN PATENT DOCUMENTS

| | | |
|---|---|---|
| KR | 1020100063011 A | 6/2010 |
| KR | 1020100083987 B1 | 7/2010 |
| KR | 1020120118680 A | 10/2012 |
| KR | 1020160052282 A | 5/2016 |

OTHER PUBLICATIONS

"Identifying Novel Drug Combinations to Overcome Treatment Resistance", National Cancer Institute, Dec. 21, 2016. 6 Pages. [URL: https://www.cancer.gov/about-cancer/treatment/research/drug-combo-resistance].

Al-Lazikani, B. et al, "Combinatorial drug therapy for cancer in the post-genomic era", Nature Biotechnology, vol. 30, No. 7, Jul. 10, 2012, pp. 679-692. 14 Pages.

* cited by examiner

FIG. 7

SINGLE-CELL ANALYSIS CHIP FOR ANTICANCER DRUG COMBINATION

TECHNICAL FIELD

The present disclosure relates to a chip for finding an anticancer drug combination appropriate for cancer cells. Specifically, the present disclosure relates to a structure of a chip for finding an anticancer drug combination appropriate for cancer cells and a method for detecting an appropriate anticancer drug combination through the chip.

BACKGROUND ART

In recent years, heterogeneity among individual cells has emerged within a homozygous cell group. As arguments of the origin of various diseases began to be discussed, the need for analysis at a single cell level has begun to emerge instead of a conventional group measurement.

Microfluidics is the study of fluid behavior in microchannels. Microfluidics can precisely control a small amount of liquid at a pico/nano liter level. Microfluidics effectively implements cell separation and arrangement techniques on microfluidic chips at a single level. Therefore, microfluidics attracts attention as a next-generation technology for single cell analysis.

These techniques are divided into passive methods using hydrodynamic force and active methods based on electrical and optical forces according to their operating mechanism. Among them, the passive methods can be operated by a simple system configuration, and thus, the passive methods have been much developed and widely used. It is a technique that can arrange cells at desired positions by considering biological cells as particles and creating traps capable of capturing particles of a specific size in a microchannel.

Conventional cancer cell capturing devices have relatively low efficiency of capturing cancer cells as single cells. Specifically, the conventional technology has performed cell lysis through diffusion of a lysis buffer for extracting protein inside cancer cells. In this case, there is a problem that a deviation occurs depending on a distance from the cell if much time is taken.

DISCLOSURE OF THE INVENTION

Technical Problem

The present disclosure provides multiple protein measurements of types and combinations of anticancer drugs at a single cell level and patient-specific drug screening platforms using the same.

Technical Solution

An analysis chip for determining an efficient anticancer drug or anticancer drug combination for cancer cells according to an embodiment of the present disclosure includes a chamber which is a unit for analyzing single cancer cells, and a plurality of valves configured to regulate a fluid to be injected into the chamber, wherein the chamber includes a channel through which a fluid including an anticancer drug and a cell lysis buffer flows, a cell sorting part configured to focus cancer cells flowing along the channel, a cell capturing part configured to focus the cancer cells focused by the cell sorting part, and an antibody array configured to capture ten types of proteins secreted from the captured cancer cells.

Advantageous Effects

A single cell analysis chip according to an embodiment of the present disclosure can provide a high-efficiency single cell capturing structure.

A single cell analysis chip according to an embodiment of the present disclosure is capable of cell lysis at a faster rate than conventional methods.

A single cell analysis chip according to an embodiment of the present disclosure can measure multiple proteins or intracellular signaling proteins secreted from a single cell through a high-density antibody array. In addition, a single cell analysis chip according to an embodiment of the present disclosure can verify the efficiency of various drugs at one time.

BRIEF DESCRIPTION OF THE DRAWINGS

As illustrated in FIG. 4(a), a high level of capturing rate can be secured through the above-described cell sorting part.

MODE FOR CARRYING OUT THE INVENTION

Hereinafter, specific embodiments of the present disclosure will be described in detail with reference to the accompanying drawings. However, the scope of the present disclosure is not limited to the following embodiments, and other regressive inventions or other embodiments included in the scope of the spirits of the present disclosure may be easily proposed through addition, change, deletion, and the like of other elements. Those skilled in the art who understand the spirit of the present disclosure can easily suggest other embodiments falling within the scope of the same idea by adding, changing, and deleting components. These embodiments also fall within the scope of the present disclosure.

In the accompanying drawings, in order to easily express the spirit of the present disclosure, small parts may not be specifically described in describing the overall structure. In describing small parts, the overall structure may not be specifically reflected. In addition, even if the specific parts such as an installation position differ, when the functions are the same, the same name is assigned thereto and the convenience of understanding can be improved. When there are a plurality of identical configurations, only one configuration will be described, the same description will be applied to the other configurations, and the description thereof will be omitted.

Figure 1:
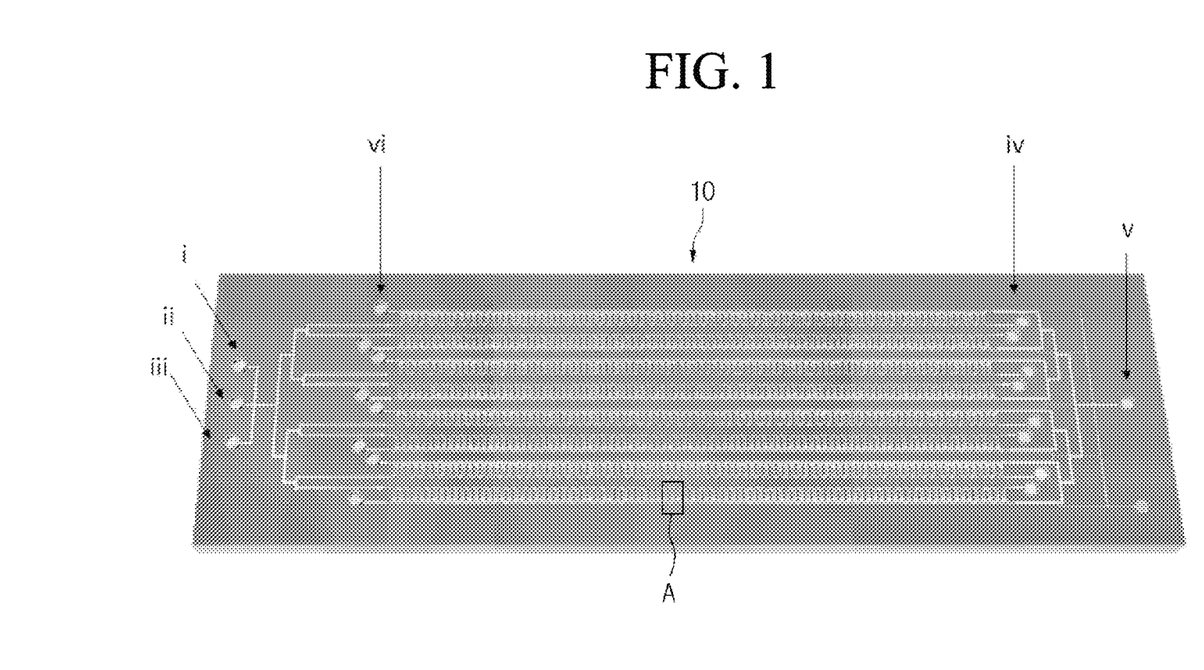
FIG. 1 illustrates an optimal anticancer drug detection system for a single cell according to an embodiment of the present disclosure.

FIG. 1 illustrates an optimal anticancer drug detection system for a single cell according to an embodiment of the present disclosure.

A single cell analysis chip 10 includes a plurality of chambers for single cell analysis. The single cell analysis chip 10 may include a plurality of channels according to the number of anticancer drugs that are combined, and the channels may include a plurality of chambers.

In the single cell analysis chip 10, i is a single cell injection part, ii is a detection antibody and fluorescent probe injection port, and iii is a portion into which a washing buffer is injected. iv is an outlet for a solution of iii. v is an injection port of a cell lysis buffer, and vi is an outlet of the cell lysis buffer. vi can also be used as an injection part when injecting multiple anticancer drugs. In this case, v is a common outlet of the anticancer drug and serves as a secreting part. In this case, the anticancer drug injected through vi may be a single anticancer drug or an anticancer drug combination product in which different anticancer drugs are combined.

Figure 2:
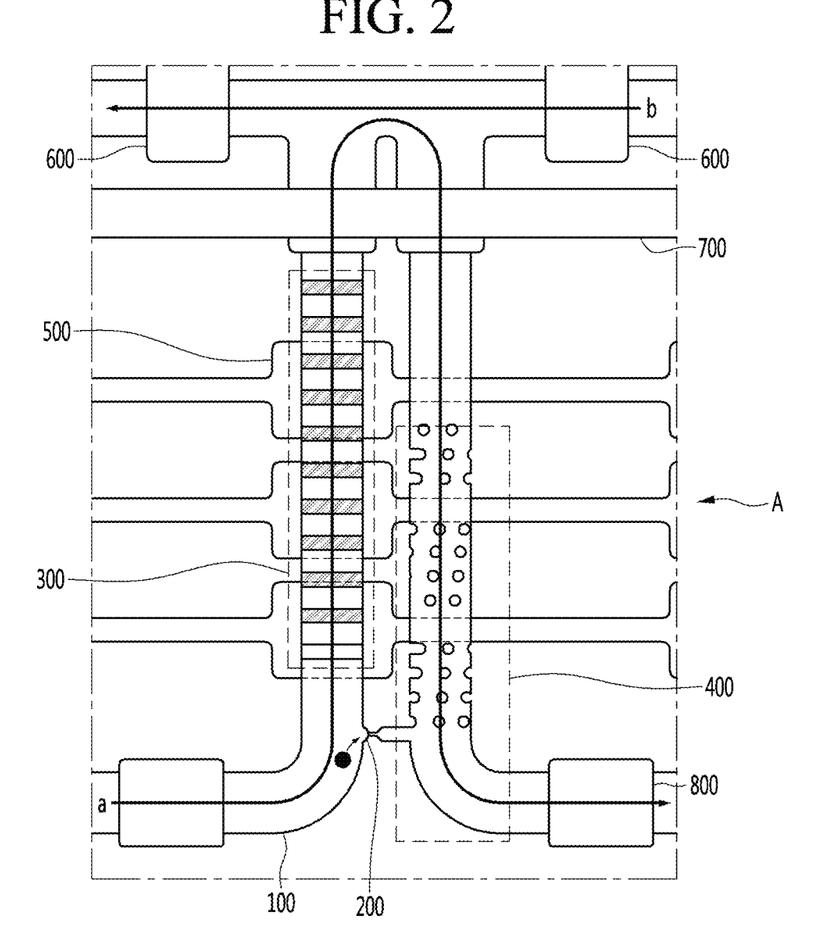
FIG. 2 illustrates a structure of a chamber constituting a single cell analysis chip.

FIG. 2 illustrates the structure of the chamber constituting the single cell analysis chip.

As illustrated in FIG. 2, a single chamber A includes a fluid channel 100, a cell capturing part 200, an antibody array 300, a cell sorting part 400, a mixing pump 500, a first valve 600, a second valve 700, and a third valve 800.

The fluid channel 100 is a channel through which a cell injection solution including cancer cells, an assay injection solution, an anticancer drug, or a cell lysis buffer passes. The fluid channel 100 includes a first channel a through which the cell injection solution or the assay injection solution flows and a second channel b through which the cell lysis buffer flows (the anticancer drug flows through the same channel, but flows in a direction opposite to the cell lysis buffer).

In the single chamber, the first channel may be divided into an upper channel and a lower channel. In the first channel a illustrated in FIG. 2, a left channel is referred to as an upper channel, and a right channel is referred to as a lower channel. The fluid channel 100 may be connected to an anticancer drug combination generation device 20 or may be connected to a cell lysis buffer supply device. Typically, the anticancer drug flows from the upper channel toward the lower channel.

The cell capturing part 200 is a part where a single cancer cell is captured. The cell capturing part 200 is provided upstream of the upper channel with respect to the fluid flow. Cancer cells moving along the channel are captured in the cell capturing part 200, and the captured cancer cells may be stained for identification.

The antibody array 300 is provided in the upper channel in the form of a barcode. The antibody array 300 may include an array provided with a plurality of different antibodies. In one embodiment, the antibody array 300 may include one reference array and ten arrays for cell analysis. At this time, fluorescent signal colors of the reference array and the cell analysis arrays are set differently so as to be identified. For the manufacture of the antibody array 300, refer to Prior Patent Document 2.

The cell sorting part 400 is provided in the lower channel. The cell sorting part 400 may include a plurality of sorting elements. In a preferred embodiment, the sorting element may have a circular shape. The description of the arrangement of the sorting elements and the specific role of the sorting elements will be further provided below, and a detailed description thereof will be omitted herein.

The mixing pump 500 is provided in the upper channel. In one embodiment, the mixing pump 500 may include three pumps and may be provided in a shape capable of pressing the upper channel. The three pumps can efficiently mix heterogeneous fluids by individual operations or an operation having a cycle. Details of the operation of the mixing pump will be further described below, and a detailed description thereof will be omitted herein.

The first valve 600, the second valve 700, and the third valve 800 regulate the flow of the fluid and serve to isolate the chamber for protein detection for the single cell. Specifically, the first valve 600 and the third valve 800 close the channel up and down based on FIG. 2 so as to isolate the chamber. A single cancer cell is captured in each chamber, and the protein generated in each cancer cell must be detected. Therefore, it is necessary to isolate the chamber.

The second valve is a valve for controlling the inflow of the cell lysis buffer. The cell lysis buffer is introduced into the chamber through the upper channel based on FIG. 2. The second valve controls the inflow of the cell lysis buffer at the upper ends of the upper and lower channels. When the second valve is opened, the cell lysis buffer is introduced into the chamber.

The configuration of the chamber A constituting the single cell analysis chip 10 has been described. Hereinafter, specific shapes of the respective chamber configurations and functions thereof will be described.

First, the cell capturing part 200 and the cell sorting part 400 will be described with reference to FIGS. 3 and 4.

Figure 3A:
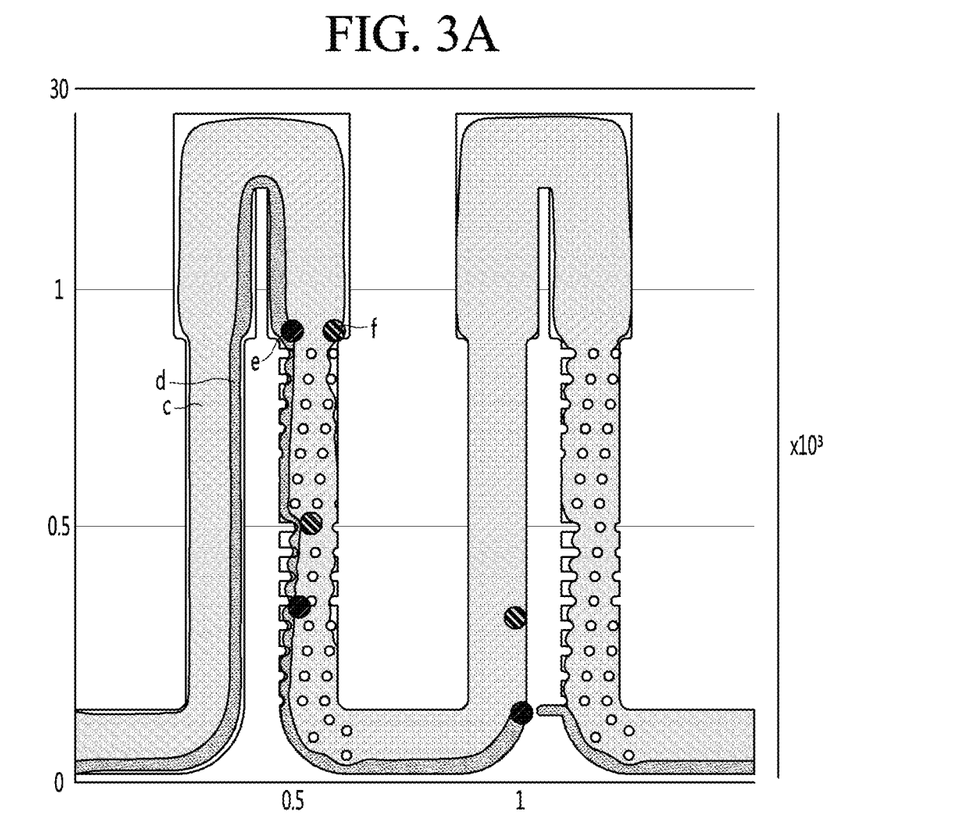
FIGS. 3(a), 3(b) and 3(c) illustrate a specific shape of a cell sorting part.
Figure 3B:
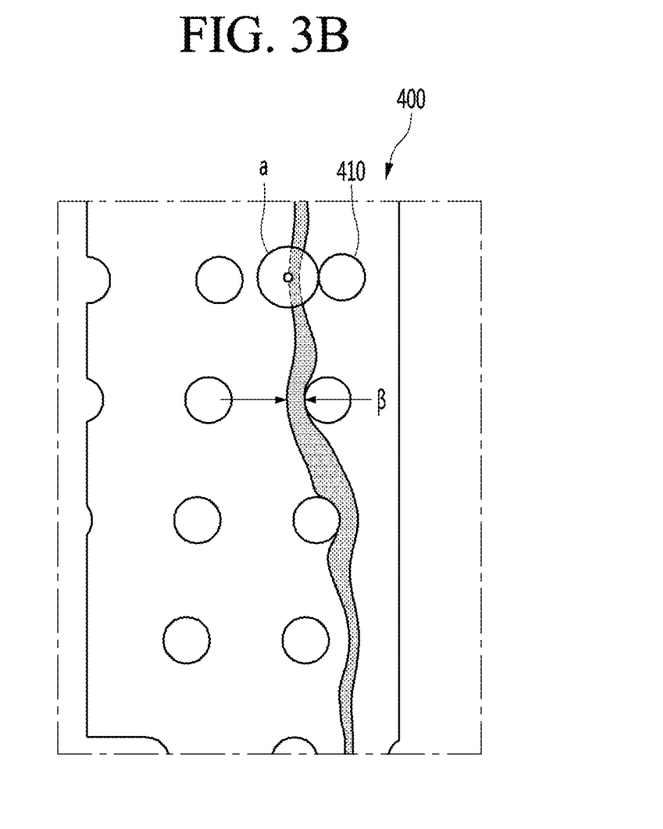
Figure 3C:
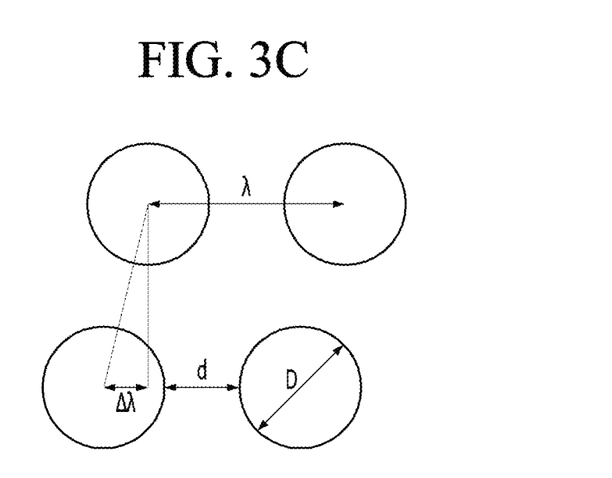

FIGS. 3(a), 3(b) and 3(c) illustrate a specific shape of the cell sorting part.

FIG. 3(a) illustrates the flow of the fluid through the cell sorting part and the movement of the particles according to the flow of the fluid.

As illustrated in FIG. 3(a), a first flow c and a second flow d exist in the above-described first channel. The first flow c is a flow that moves first particles e captured by the cell capturing part, and the second flow d is a flow that moves second particles f which are not captured by the cell capturing part.

As illustrated in FIG. 3(a), when the first particles e and the second particles f are injected into the channel, the flow of particles is guided into the inside of the channel by the cell sorting part 400. However, the first particles e are injected along the first flow c when initially injected. Therefore, the first particles e are captured in the cell capturing part 200 in preference to the second particles f. The second particles f are induced into the channel by the cell sorting part 200. However, when initially injected, the second particles f are injected along the second flow d. Therefore, a capturing priority may be degraded as compared to the first particles. However, since the second particles f move along the first flow for a next cell capturing part, the second particles f are captured with a high probability.

FIGS. 3(b) and 3(c) illustrate the specific design of the cell sorting part for guiding particle movement described with reference to FIG. 3(a).

As illustrated in FIG. 3(b), the cell sorting part 400 includes a plurality of sorting elements 410. In a preferred embodiment, the sorting elements 410 have a circular shape. At this time, the sorting elements are arranged diagonally at regular intervals. The sorting elements formed diagonally in an inner direction of the channel serve to guide the flow of the particles a (e.g., cancer cells) into the channel.

An appropriate distance between the sorting elements will be described below.

As the interval between the sorting elements is wider, the flow of particles may be facilitated. However, the wide interval between the sorting elements is not necessarily good. As the interval between the sorting elements is wider, particles are less guided into the channel, and thus, the sorting elements may not perform their functions well.

Therefore, it is important to determine the appropriate distance between the sorting elements.

FIG. 3(b) illustrates the fluid flow when a plurality of sorting elements are provided in the channel. When the fluid is divided into two parts by the sorting element, a critical streamline β is defined from a circular element. A relationship between the sorting elements 410 must be defined in order for the particles to be focused (meaning moving along a good flow (first flow) to be guided inside the channel and captured in the cell capturing part). Specifically, the relationship between the sorting elements 410 must be designed such that a Dc value is smaller than that of the cancer cells to be focused. In general, Dc is approximated twice the critical streamline from the circular element, and a specific Dc value can be obtained through Equation 1.

$$D_c = 1.4 \times G \times N^{-0.48}$$ [Equation 1]

G is λ–D, and λ and D are defined in FIG. 3(c). N is λ/Δλ.

As a result, the interval between the sorting elements must be greater than the size of the largest cancer cell and the Dc value must be smaller than the size of the smallest cancer cell.

Figure 4A:
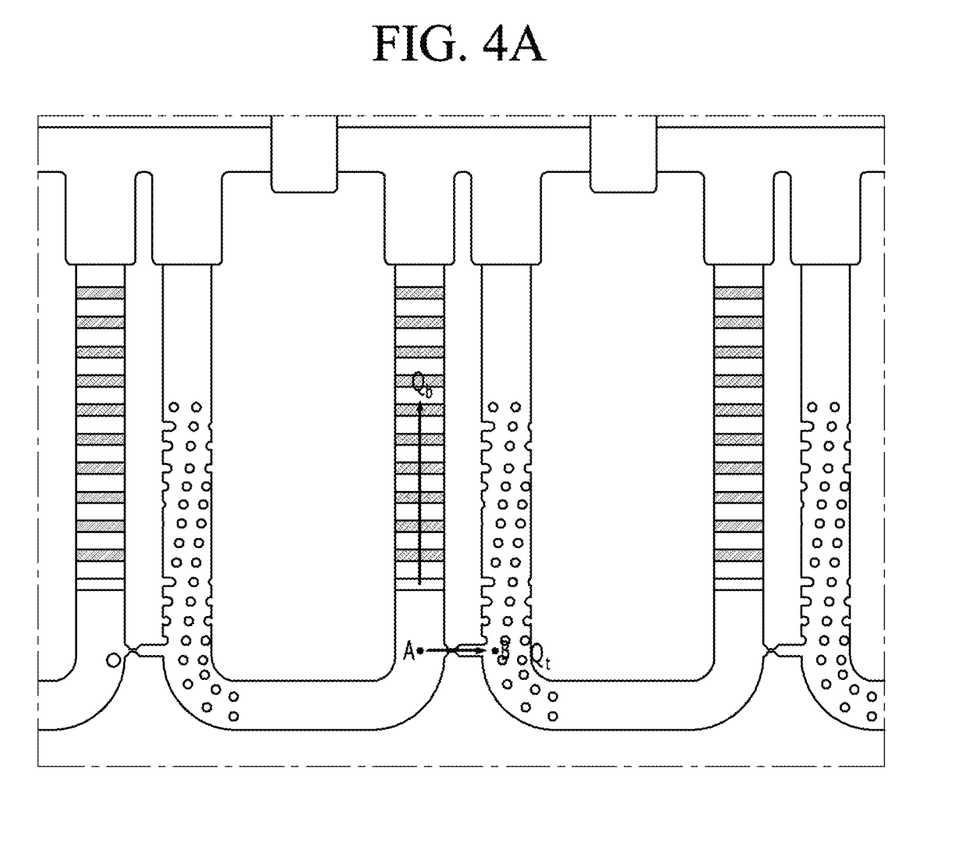
FIGS. 4(a) and 4(b) illustrate a capturing rate according to the number of captured cells.
Figure 4B:
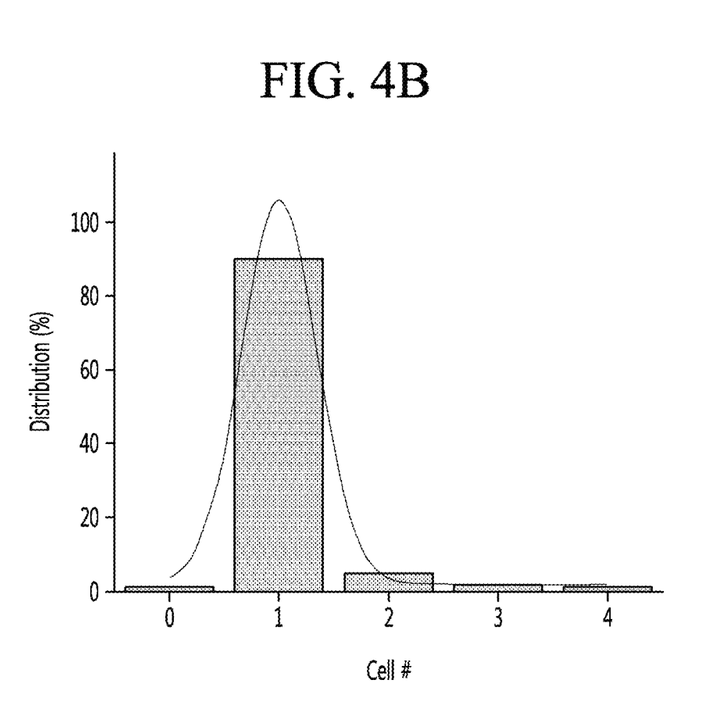

FIGS. 4(a) and 4(b) illustrate the design of the cell capturing part for single cell capture and the capturing rate.

FIG. 4(a) illustrates a specific shape of the cell capturing part 200. The cell capturing part 200 is configured to automatically capture cells flowing in sorting through the cell sorting part 400. To this end, the cell capturing part has a structure that connects the upper channel to the lower channel. Due to this structure, a first flow through the cell capturing part and a second flow bypassing the cell capturing part are formed in the fluid channel.

At this time, in order to efficiently capture the single cell, the first flow needs to have the same size as the single cell size. Therefore, it is important to determine the ratio of the flow rate of the first flow to the flow rate of the second flow for this purpose.

As illustrated in FIG. 4(a), there are points A and B, and the flow rate Qt of the first flow and the flow rate Qb of the second flow are defined. A hydraulic pressure drop between the point A and the point B is expressed by Equation 2.

$$\text{TRIANGLE}_{AB} = QR$$ [Equation 2]

R is a fluid resistance and is expressed by Equation 3.

$$R = \frac{12 \, \mu L}{wh^3 \left(1 - 0.63 \frac{h}{w}\right)}$$ [Equation 3]

w is the width of the channel, h is the height of the channel, L is the length of the channel, and • is the fluid viscosity.

At this time, the hydraulic drop value from the point A to the point B can be seen to be the same in the first flow and the second flow, and Equation 4 is established.

$$Q_b R_b = Q_t R_t$$ [Equation 4]

Equation 4 may be summarized as Equation 5.

$$Q_b / Q_t = R_t / R_b$$ [Equation 5]

As a result, in order for the cell capturing part to capture the single cell well, the ratio of the flow rate of the first flow to the flow rate of the second flow must be adjusted to correspond to the single cell size. The ratio of the flow rate of the first flow to the flow rate of the second flow is the result showing the capturing rate according to the number of captured cells through the adjustment of the width, length, height, or viscosity of the channel. As illustrated in FIG. 4(b), it is possible to ensure a high level of capturing rate through the above-described cell sorting part.

Figure 5A:
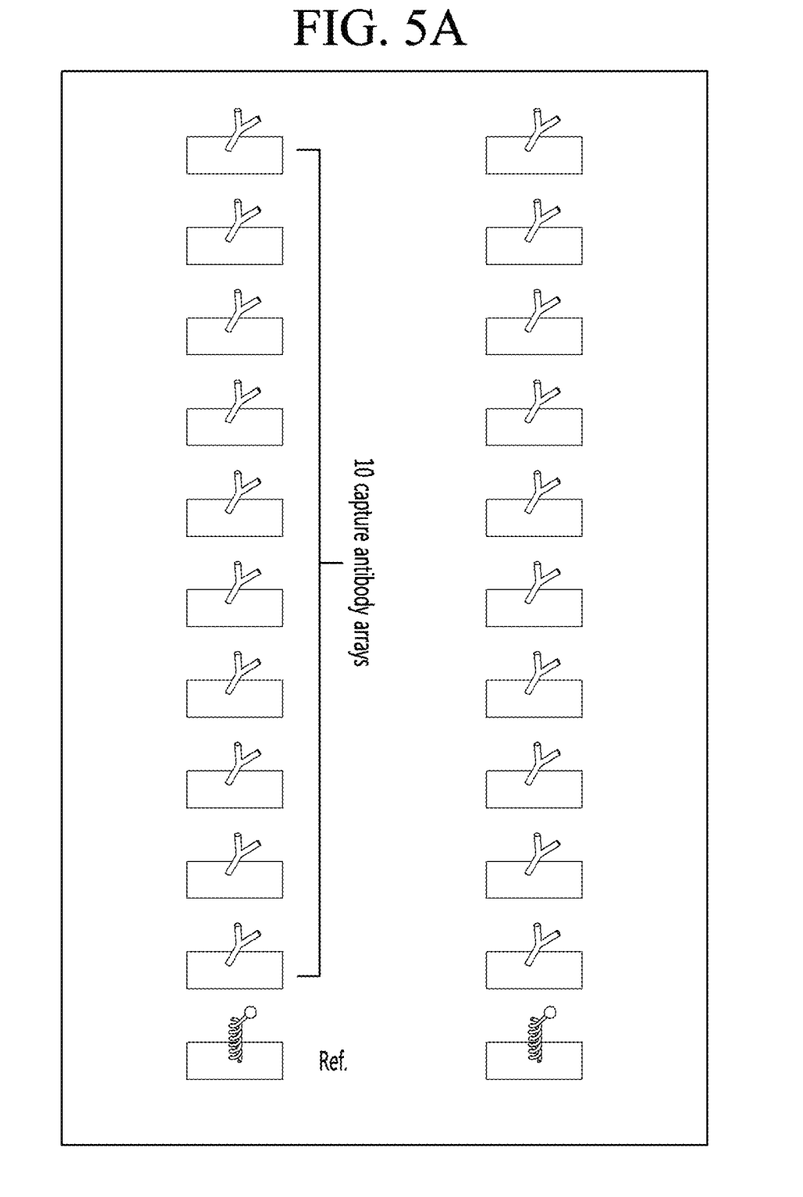
FIGS. 5(a) and 5(b) illustrate a specific shape of an antibody array.
Figure 5B:
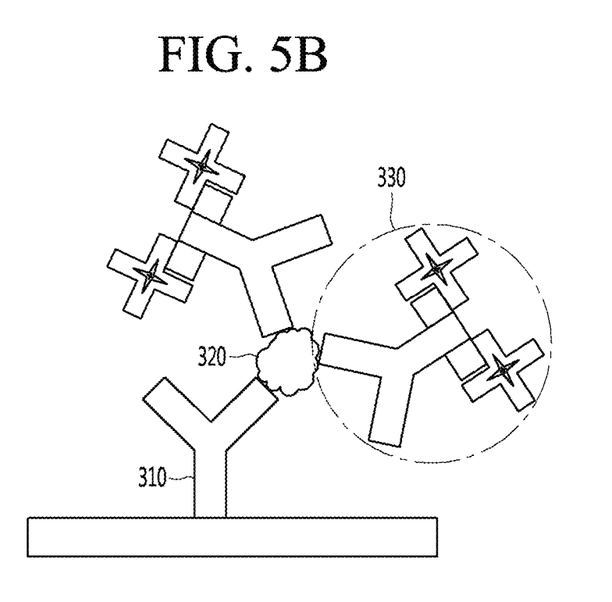

FIGS. 5(a), 5(b) and 5(c) illustrate the specific shape of the antibody array and the final assay.

As illustrated in FIG. 5(a), the antibody array 300 may include a reference array and a capturing array. The reference array may use any probe capable of emitting a fluorescent signal regardless of a protein emitted by a cancer cell. However, for signal identification, the fluorescent color of the reference array must be different from the fluorescent color of the capturing array for measuring the protein of the cancer cell.

The capturing array may be an array provided with a plurality of different antibodies. In a preferred embodiment, the capturing array can include ten arrays, that is, three arrays for detecting the protein before the cancer cell lyses by the cell lysis buffer and seven arrays for detecting the protein after the cancer cell lyses.

FIG. 5(b) illustrates the final assay in which a shape marker is attached to the captured protein for analysis through the analyzer.

An antibody 310 is first attached to the capturing array. A protein 320 emitted through the antibody or cell lysis buffer processing is bonded to the attached antibody. A fluorescent marker 330 is attached to the protein so as to analyze the captured protein.

In a specific embodiment, when all proteins are combined through the capturing array, biotinylated detection antibody is injected so as to detect ten types of proteins, and streptavidin-Cy5 (fluorochromosome) is injected so as to obtain a fluorescent signal, thereby forming the final assay for obtaining the fluorescent signal.

An efficient anticancer drug combination can be selected for the patient based on the protein captured in the antibody array 300 and the finally obtained fluorescent signal. The type of the protein secreted when an anticancer drug works on a particular cancer cell is known from previous studies. In this manner, the protein captured in the antibody array 300 can be analyzed to determine the efficient anticancer drug combination for the patient.

Figure 6A:
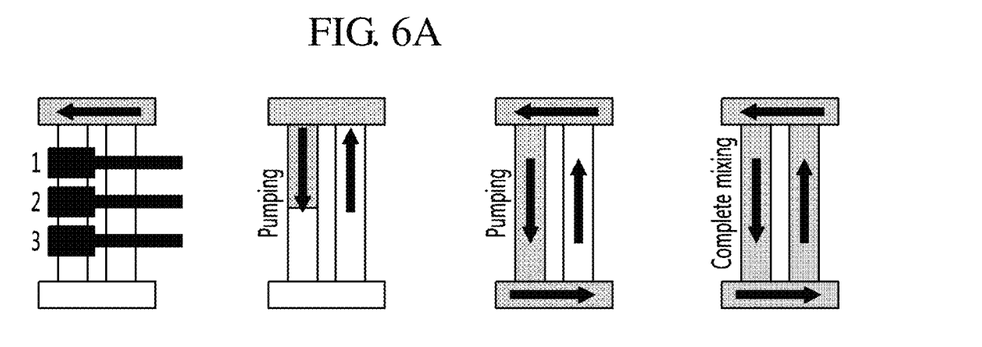
FIGS. 6(a) and 6(b) illustrate an operation of a mixing pump.
Figure 6B:
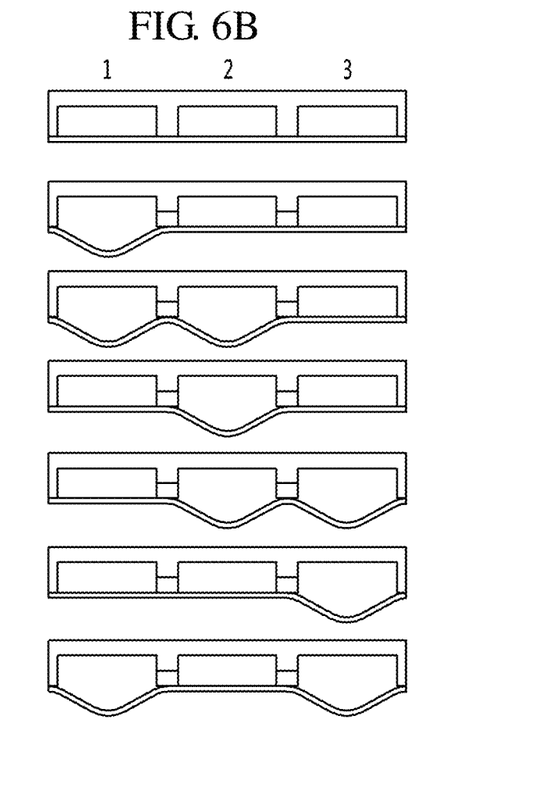

FIGS. 6(a) and 6(b) illustrate the operation of the mixing pump.

As illustrated in FIG. 6(a), the mixing pump 600 is provided to press the upper channel. When fluid (cell lysis buffer or washing fluid) is injected into the channel, the fluid is first injected into the upper channel by the operation of the mixing pump 600 as illustrated in FIG. 6(a). The fluid is circulated and mixed in the order shown in FIG. 6(a) through the continuous operation of the mixing pump 600.

FIG. 6(b) illustrates an example of the operation of the mixing pump including three pumps. In one embodiment of the present disclosure, the mixing pump 600 may operate as illustrated in FIG. 6(b) to circulate and mix the fluid.

Figure 7:
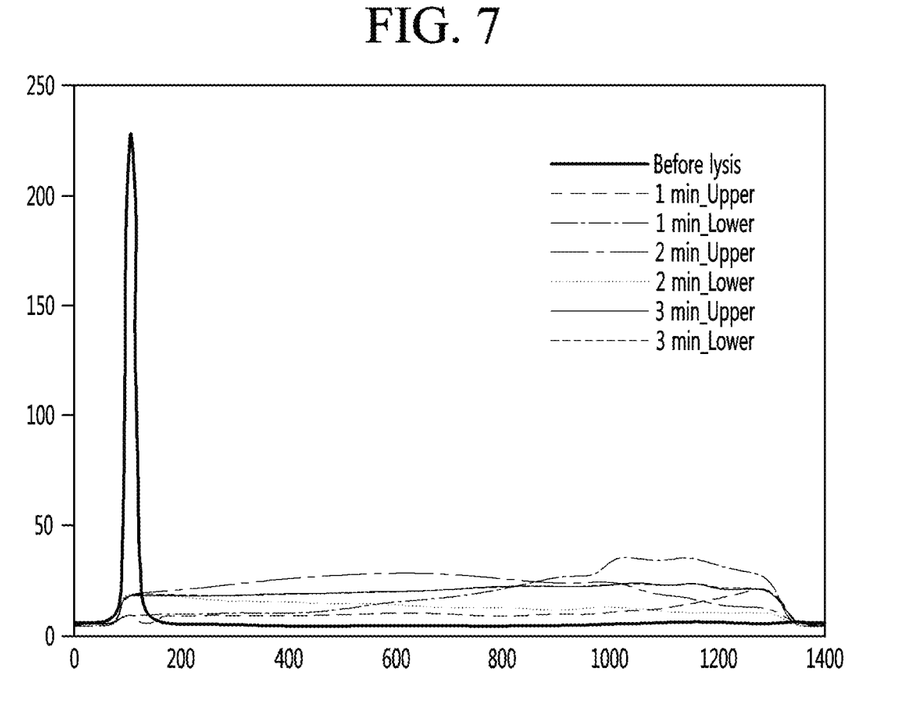
FIG. 7 illustrates fluorescent signal measurement results analyzed along channels before and after cell lysis.

FIG. 7 illustrates fluorescent signal measurement results analyzed along channels before and after cell lysis. As in the result of FIG. 7, it can be seen that the cell lysis material is uniformly spread over time.

Figure 8:
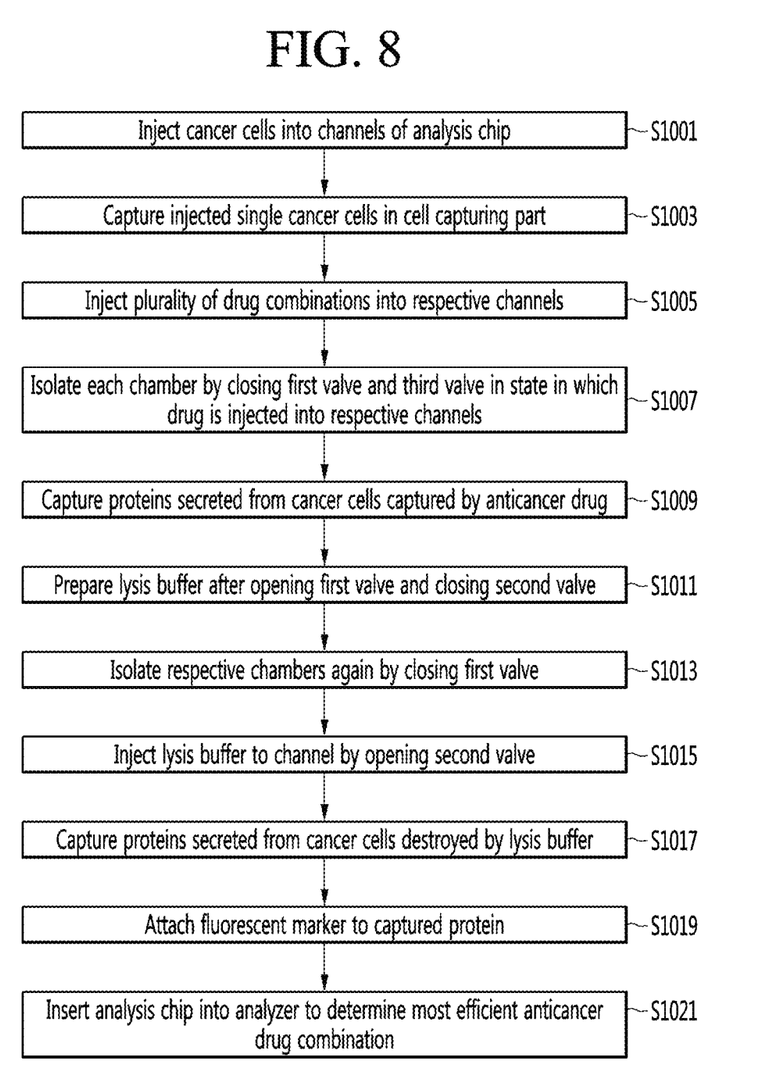
FIG. 8 is a flowchart illustrating an analysis method through a single cell analysis chip for an anticancer drug combination according to an embodiment of the present disclosure.

FIG. 8 is a flowchart illustrating an analysis method through a single cell analysis chip for an anticancer drug combination according to an embodiment of the present disclosure.

The cancer cell is injected into the channel of the analysis chip (S1001). In this case, the injected cancer cell may be a cancer cell of a cancer patient who wants to know an efficient anticancer drug combination.

The injected cancer cell is captured in the cell capturing part in the course of flowing through the channel (S1003). The cancer cell passes through the plurality of chambers and is focused by the cell sorting parts included in the chambers. The focused cancer cell is captured in the cell trapper in the form of a single cell. At this time, the captured cancer cell can be stained for identification.

The anticancer drugs mixed in different combinations are injected into the plurality of channels of the analysis chip (S1005). The anticancer drugs mixed in different combinations are injected through different channels.

Each drug is completely injected into the channel, and the first valve and the third valve are closed to isolate the chamber (S1007). As described above, the chamber is a test unit for determining an appropriate anticancer drug for each single cancer cell. The channel prevents errors in the test results due to the mixing of the proteins from different cancer cells.

The protein secreted from the cancer cell captured by the anticancer drug is captured (S1009). The cancer cell can secrete certain proteins through the operation with the anticancer drug. In this case, the secreted protein may be a criterion for determining whether an anticancer drug is suitable. The protein secreted from the cancer cell is captured in the antibody array.

When the capturing of the protein secreted before the cell lysis is completed, the first valve is opened, the second valve is closed, and the cell lysis buffer is prepared (S1011). The second valve is a valve capable of closing the upper channel and the lower channel in the chamber at one time. At this time, the third valve is kept closed. The first valve may be opened to prepare for injection of the cell lysis buffer into all chambers.

After the preparation of the cell lysis buffer is completed, the first valve is closed again to isolate the chamber (S1013). As in operation S1007, the chambers are isolated so that proteins secreted from the cancer cells captured in the chambers do not mix with each other.

The second valve is opened in a state in which the chamber is isolated, and the cell lysis buffer is injected into the chamber (S1015). The cell lysis buffer acts on the cancer cell and breaks down a membrane of the cancer cell to lyse the cancer cell. At this time, the cell lysis buffer can be rapidly diffused through the mixing pump.

The protein secreted from the cancer cell destroyed by the cell lysis buffer is captured (S1017). As in operation S1009, the secreted protein is captured by the antibody array. In addition, the protein secreted by the destruction of the cancer cell that have been exposed to the efficient anticancer drug is known from the previous studies. The protein captured at this time may also be another criterion for determining the efficient anticancer drug.

When the protein capturing is completed, a fluorescent marker for obtaining a fluorescent signal is attached to the captured protein (S1019). Specifically, a fluorescent marker (e.g., biotinylated detection antibody and streptavidin-Cy5) is injected to obtain a fluorescent signal, and the injected fluorescent marker is combined with the captured protein to form the final assay.

The assay chip including the plurality of antibody arrays in which the final assay is formed is inserted into the analyzer to determine the most efficient anticancer drug combination (S1021). As described above, the previous studies have shown that there is a difference between the protein secreted by the cancer cell exposed to the efficient anticancer drug and the protein secreted by the cancer cell not exposed to the efficient anticancer drug. By using this, it is possible to determine the most efficient anticancer drug combination for the patient under test.

In this case, the fluorescent signal may be measured through the fluorescent marker attached to a protein captured in the antibody array. The measured fluorescent signal may represent the captured protein, and the single cell-based multiple protein measurement and signal acquisition are possible through the multiple immunoassay based on the fluorescent signal.

The present disclosure may be embodied as computer-readable codes on a program-recorded medium. The computer-readable recording medium may be any recording medium that can store data which can be thereafter read by a computer system. Examples of the computer-readable medium may include a hard disk drive (HDD), a solid state disk (SSD), a silicon disk drive (SDD), a ROM, a RAM, a CD-ROM, a magnetic tape, a floppy disk, and an optical data storage device. The computer may also include the processor 180 of the artificial intelligence apparatus. Therefore, the detailed description should not be construed as limiting in all aspects and should be considered as illustrative. The scope of the present disclosure should be determined by reasonable interpretation of the appended claims, and all changes within the equivalent scope of the present disclosure falls within the scope of the present disclosure.

The invention claimed is:

1. An analysis method comprising:
   injecting cancer cells of a patient to be analyzed into an analysis chip, the analysis chip comprising:
   a chamber which is a unit for analyzing single cancer cells; and
   a plurality of valves configured to regulate a fluid to be injected into the chamber, wherein the chamber comprises:
     a channel through which a fluid including an anticancer drug and a cell lysis buffer flows;
     a cell sorting part configured to focus cancer cells flowing along the channel;
     a cell capturing part configured to capture the cancer cells focused by the cell sorting part; and
     an antibody array configured to capture proteins secreted from the captured cancer cells;
   sorting the injected single cancer cells on one channel wall and capturing the injected single cancer cells by a cell capturing part;
   injecting a plurality of drug combinations into respective channels constituting the analysis chip;
   isolating the chamber by closing a first valve of the plurality of valves in a state in which the drug is injected into each channel, wherein the first valve configured to open or closing the chamber;
   capturing first proteins secreted by the captured cancer cells in a reaction with the anticancer drug;
   opening the first valve and closing a second valve before the cell lysis is completed, wherein the second valve is configured to control the inflow of the cell lysis buffer into the chamber;
   closing the first valve to isolate the chamber after the preparation of the cell lysis buffer is completed;

opening the second valve and injecting a cell lysis buffer to destroy the cancer cells;

capturing second proteins secreted from cancer cells destroyed by the cell lysis buffer wherein the first proteins differ from the second proteins; and inserting the analysis chip including the antibody array in which protein is captured into an analyzer to determine a most efficient anticancer drug or anticancer drug combination for the patient, wherein the first proteins and the second proteins are captured by the antibody array.

2. The analysis method of claim 1, further comprising connecting a fluorescent probe to the protein captured in the antibody array, wherein the determining of the most efficient anticancer drug or anticancer drug combination for the patient comprises determining the most efficient anticancer drug or anticancer drug combination based on a fluorescent signal capable of being measured by the fluorescent probe.

3. The method of claim 1, wherein the chamber further comprises a microfluidic-based mixing pump configured to promote diffusion of the cell lysis buffer and simultaneous single cell lysis.

4. The method of claim 1, wherein the cell sorting part comprises a plurality of sorting elements configured to focus the cancer cells, and the plurality of sorting elements are arranged diagonally based on a flow of the anticancer drug.

5. The method of claim 4, wherein the plurality of sorting elements are arranged at specific intervals, and the specific interval is determined based on a size of a cancer cell to be tested and a size of the sorting element.

6. The method of claim 5, wherein the sorting element has a circular shape.

7. The method of claim 1, wherein the antibody array comprises a first array configured to capture the first proteins secreted before the cancer cells are destroyed by the cell lysis buffer, and a second array that captures all proteins including the second proteins secreted after the cancer cells are destroyed by the cell lysis buffer.

8. The method of claim 7, wherein the antibody array further comprises a reference array configured to generate a fluorescent signal independent of the proteins secreted by the cancer cells.

* * * * *